(12) United States Patent
Yang et al.

(10) Patent No.: US 7,829,328 B2
(45) Date of Patent: Nov. 9, 2010

(54) ASSAY DEVICES THAT UTILIZE HOLLOW PARTICLES

(75) Inventors: Kaiyuan Yang, Cumming, GA (US); Ning Wei, Roswell, GA (US); Rosann Kaylor, Cumming, GA (US); Chibueze Obinna Chidebelu-Eze, Atlanta, GA (US); Zdravko Savov Atanassov, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 712 days.

(21) Appl. No.: 11/440,956

(22) Filed: May 25, 2006

(65) Prior Publication Data

US 2006/0216834 A1     Sep. 28, 2006

Related U.S. Application Data

(62) Division of application No. 10/406,577, filed on Apr. 3, 2003.

(51) Int. Cl.
*C12M 1/34* (2006.01)
(52) U.S. Cl. .............. 435/288.7; 435/286.5; 435/287.7; 436/528; 436/533; 436/535; 427/2.11; 427/2.13
(58) Field of Classification Search .................. 436/533, 436/534, 514; 435/7.34, 36
See application file for complete search history.

(56) References Cited

U.S. PATENT DOCUMENTS

| | | | |
|---|---|---|---|
| 4,094,647 A | 6/1978 | Deutsch et al. | |
| 4,110,529 A | 8/1978 | Stoy | |
| 4,168,146 A | 9/1979 | Grubb et al. | |
| RE30,267 E | 5/1980 | Bruschi | |
| 4,210,723 A | 7/1980 | Dorman et al. | |
| 4,235,601 A | 11/1980 | Deutsch et al. | |
| 4,275,149 A | 6/1981 | Litman et al. | |
| 4,312,228 A | 1/1982 | Wohltjen | |
| 4,361,537 A | 11/1982 | Deutsch et al. | |
| 4,363,874 A | 12/1982 | Greenquist | |
| 4,366,241 A | 12/1982 | Tom et al. | |
| 4,374,925 A | 2/1983 | Litman et al. | |
| 4,385,126 A | 5/1983 | Chen et al. | |

(Continued)

FOREIGN PATENT DOCUMENTS

| | | |
|---|---|---|
| EP | 0073593 A1 | 3/1983 |
| EP | 0205698 A1 | 12/1986 |
| EP | 0420053 A1 | 4/1991 |
| EP | 0437287 B1 | 7/1991 |
| EP | 0462376 B1 | 12/1991 |

(Continued)

OTHER PUBLICATIONS

*Magnetic Microparticles*, Polysciences, Inc. Technical Data Sheet 438, 2 pages.

(Continued)

*Primary Examiner*—Nelson Yang
(74) *Attorney, Agent, or Firm*—Dority & Manning, P.A.

(57) ABSTRACT

Hollow particles for use in various types of assay devices are provided. Due to their hollow or voided structure, the particles may exhibit a variety of beneficial properties. For instance, hollow particles are generally lightweight, and thus, relatively inexpensive in comparison to other types of particles. Hollow particles may also form a stable system without requiring refrigeration or rotation. In addition, hollow particles may possess enhanced light diffraction capabilities, which may be particularly beneficial in certain types of assay devices, e.g., diffraction-based assay devices.

14 Claims, 4 Drawing Sheets

U.S. PATENT DOCUMENTS

| | | | |
|---|---|---|---|
| 4,426,451 A | 1/1984 | Columbus | |
| 4,427,836 A | 1/1984 | Kowalski et al. | |
| 4,435,504 A | 3/1984 | Zuk et al. | |
| 4,441,373 A | 4/1984 | White | |
| 4,442,204 A | 4/1984 | Greenquist et al. | |
| 4,444,592 A | 4/1984 | Ludwig | |
| 4,477,635 A | 10/1984 | Mitra | |
| 4,480,042 A | 10/1984 | Craig et al. | |
| 4,533,499 A | 8/1985 | Clark et al. | |
| 4,533,629 A | 8/1985 | Litman et al. | |
| 4,534,356 A | 8/1985 | Papadakis | |
| 4,537,861 A | 8/1985 | Elings et al. | |
| 4,540,659 A | 9/1985 | Litman et al. | |
| 4,552,458 A | 11/1985 | Lowne | |
| 4,561,286 A | 12/1985 | Sekler et al. | |
| 4,562,157 A | 12/1985 | Lowe et al. | |
| 4,595,661 A | 6/1986 | Cragle et al. | |
| 4,596,697 A | 6/1986 | Ballato | |
| 4,614,723 A | 9/1986 | Schmidt et al. | |
| 4,661,235 A | 4/1987 | Krull et al. | |
| 4,698,262 A | 10/1987 | Schwartz et al. | |
| 4,703,017 A * | 10/1987 | Campbell et al. | 436/501 |
| 4,722,889 A | 2/1988 | Lee et al. | |
| 4,727,019 A | 2/1988 | Valkirs et al. | |
| 4,731,337 A | 3/1988 | Luotola et al. | |
| 4,743,542 A | 5/1988 | Graham, Jr. et al. | |
| 4,776,944 A | 10/1988 | Janata et al. | |
| 4,837,168 A | 6/1989 | de Jaeger et al. | |
| 4,842,783 A | 6/1989 | Blaylock | |
| 4,843,000 A | 6/1989 | Litman et al. | |
| 4,843,021 A | 6/1989 | Noguchi et al. | |
| 4,844,613 A | 7/1989 | Batchelder et al. | |
| 4,849,338 A | 7/1989 | Litman et al. | |
| 4,855,240 A | 8/1989 | Rosenstein et al. | |
| 4,857,453 A | 8/1989 | Ullman et al. | |
| 4,877,586 A | 10/1989 | Devaney, Jr. et al. | |
| 4,877,747 A | 10/1989 | Stewart | |
| 4,895,017 A | 1/1990 | Pyke et al. | |
| 4,916,056 A | 4/1990 | Brown, III et al. | |
| 4,917,503 A | 4/1990 | Bhattacharjee | |
| 4,940,734 A | 7/1990 | Ley et al. | |
| 4,963,498 A | 10/1990 | Hillman et al. | |
| 4,973,670 A | 11/1990 | McDonald et al. | |
| 4,992,385 A | 2/1991 | Godfrey | |
| 4,997,772 A * | 3/1991 | Sutton et al. | 436/533 |
| 5,003,178 A | 3/1991 | Livesay | |
| 5,023,053 A | 6/1991 | Finlan | |
| 5,026,653 A | 6/1991 | Lee et al. | |
| 5,035,863 A | 7/1991 | Finlan et al. | |
| 5,055,265 A | 10/1991 | Finlan | |
| 5,063,081 A | 11/1991 | Cozzette et al. | |
| 5,064,619 A | 11/1991 | Finlan | |
| 5,075,077 A | 12/1991 | Durley, III et al. | |
| 5,076,094 A | 12/1991 | Frye et al. | |
| 5,096,671 A | 3/1992 | Kane et al. | |
| 5,114,676 A | 5/1992 | Leiner et al. | |
| 5,120,662 A | 6/1992 | Chan et al. | |
| 5,124,254 A | 6/1992 | Hewlins et al. | |
| 5,134,057 A | 7/1992 | Kuypers et al. | |
| 5,137,609 A | 8/1992 | Manian et al. | |
| 5,143,854 A | 9/1992 | Pirrung et al. | |
| 5,145,784 A | 9/1992 | Cox et al. | |
| 5,152,758 A | 10/1992 | Kaetsu et al. | |
| 5,156,953 A | 10/1992 | Litman et al. | |
| 5,182,135 A | 1/1993 | Giesecke et al. | |
| 5,196,350 A | 3/1993 | Backman et al. | |
| 5,200,084 A | 4/1993 | Liberti et al. | |
| 5,221,454 A | 6/1993 | Manian et al. | |
| 5,225,935 A | 7/1993 | Watanabe et al. | |
| 5,234,813 A | 8/1993 | McGeehan et al. | |
| 5,235,238 A | 8/1993 | Nomura et al. | |
| 5,238,815 A | 8/1993 | Higo et al. | |
| 5,242,828 A | 9/1993 | Bergström et al. | |
| 5,252,459 A | 10/1993 | Tarcha et al. | |
| 5,262,299 A | 11/1993 | Evangelista et al. | |
| 5,268,306 A | 12/1993 | Berger et al. | |
| 5,314,923 A | 5/1994 | Cooke et al. | |
| 5,316,727 A | 5/1994 | Suzuki et al. | |
| 5,320,944 A | 6/1994 | Okada et al. | |
| 5,321,492 A | 6/1994 | Detwiler et al. | |
| 5,327,225 A | 7/1994 | Bender et al. | |
| 5,330,898 A | 7/1994 | Bar-Or et al. | |
| 5,342,759 A | 8/1994 | Litman et al. | |
| 5,352,582 A | 10/1994 | Lichtenwalter et al. | |
| 5,356,782 A | 10/1994 | Moorman et al. | |
| 5,358,852 A | 10/1994 | Wu | |
| 5,369,717 A | 11/1994 | Attridge | |
| 5,374,563 A | 12/1994 | Maule | |
| 5,376,255 A | 12/1994 | Gumbrecht et al. | |
| 5,387,503 A | 2/1995 | Selmer et al. | |
| 5,395,754 A | 3/1995 | Lambotte et al. | |
| 5,415,842 A | 5/1995 | Maule | |
| 5,418,136 A | 5/1995 | Miller et al. | |
| 5,424,219 A | 6/1995 | Jirikowski | |
| 5,432,057 A | 7/1995 | Litman et al. | |
| 5,436,161 A | 7/1995 | Bergström et al. | |
| 5,445,971 A | 8/1995 | Rohr | |
| 5,451,683 A | 9/1995 | Barrett et al. | |
| 5,455,475 A | 10/1995 | Josse et al. | |
| 5,464,741 A | 11/1995 | Hendrix | |
| 5,467,778 A | 11/1995 | Catt et al. | |
| 5,468,606 A | 11/1995 | Bogart et al. | |
| 5,482,830 A | 1/1996 | Bogart et al. | |
| 5,482,867 A | 1/1996 | Barrett et al. | |
| 5,484,867 A | 1/1996 | Lichtenhan et al. | |
| 5,489,678 A | 2/1996 | Fodor et al. | |
| 5,489,988 A | 2/1996 | Ackley et al. | |
| 5,492,840 A | 2/1996 | Malmqvist et al. | |
| 5,500,350 A | 3/1996 | Baker et al. | |
| 5,504,013 A | 4/1996 | Senior | |
| 5,508,171 A | 4/1996 | Walling et al. | |
| 5,510,481 A | 4/1996 | Bednarski et al. | |
| 5,512,131 A | 4/1996 | Kumar et al. | |
| 5,514,559 A | 5/1996 | Markert-Hahn et al. | |
| 5,514,785 A | 5/1996 | Van Ness et al. | |
| 5,516,635 A | 5/1996 | Ekins et al. | |
| 5,518,689 A | 5/1996 | Dosmann et al. | |
| 5,518,883 A | 5/1996 | Soini | |
| 5,527,711 A | 6/1996 | Tom-Moy et al. | |
| 5,534,132 A | 7/1996 | Vreeke et al. | |
| 5,554,541 A | 9/1996 | Malmqvist et al. | |
| 5,569,608 A | 10/1996 | Sommer | |
| 5,571,684 A | 11/1996 | Lawrence et al. | |
| 5,573,909 A | 11/1996 | Singer et al. | |
| 5,585,279 A | 12/1996 | Davidson | |
| 5,589,401 A | 12/1996 | Hansen et al. | |
| 5,591,581 A | 1/1997 | Massey et al. | |
| 5,596,414 A | 1/1997 | Tyler | |
| 5,599,668 A | 2/1997 | Stimpson et al. | |
| 5,618,888 A | 4/1997 | Choi et al. | |
| 5,620,850 A | 4/1997 | Bamdad et al. | |
| 5,637,509 A | 6/1997 | Hemmilä et al. | |
| 5,647,994 A | 7/1997 | Tuunanen et al. | |
| 5,658,443 A | 8/1997 | Yamamoto et al. | |
| 5,663,213 A | 9/1997 | Jones et al. | |
| 5,670,381 A | 9/1997 | Jou et al. | |
| 5,672,256 A | 9/1997 | Yee | |
| 5,700,636 A | 12/1997 | Sheiness et al. | |
| 5,726,064 A | 3/1998 | Robinson et al. | |
| 5,731,147 A | 3/1998 | Bard et al. | |
| 5,736,188 A | 4/1998 | Alcock et al. | |
| 5,753,517 A | 5/1998 | Brooks et al. | |
| 5,770,416 A | 6/1998 | Lihme et al. | |
| 5,780,308 A | 7/1998 | Ching et al. | |

| | | | |
|---|---|---|---|
| 5,795,470 A | 8/1998 | Wang et al. |
| 5,795,543 A | 8/1998 | Poto et al. |
| 5,811,526 A | 9/1998 | Davidson |
| 5,827,748 A | 10/1998 | Golden |
| 5,834,226 A | 11/1998 | Maupin |
| 5,837,429 A | 11/1998 | Nohr et al. |
| 5,837,546 A | 11/1998 | Allen et al. |
| 5,843,692 A | 12/1998 | Phillips et al. |
| 5,852,229 A | 12/1998 | Josse et al. |
| 5,876,944 A | 3/1999 | Kuo |
| 5,885,527 A | 3/1999 | Buechler |
| 5,906,921 A | 5/1999 | Ikeda et al. |
| 5,910,447 A | 6/1999 | Lawrence et al. |
| 5,910,940 A | 6/1999 | Guerra |
| 5,922,537 A | 7/1999 | Ewart et al. |
| 5,922,550 A | 7/1999 | Everhart et al. |
| 5,951,492 A | 9/1999 | Douglas et al. |
| 5,962,995 A | 10/1999 | Avnery |
| 6,004,530 A | 12/1999 | Sagner et al. |
| 6,020,047 A | 2/2000 | Everhart |
| 6,027,904 A | 2/2000 | Devine et al. |
| 6,027,944 A | 2/2000 | Robinson et al. |
| 6,030,792 A | 2/2000 | Otterness et al. |
| 6,030,840 A | 2/2000 | Mullinax et al. |
| 6,033,574 A | 3/2000 | Siddiqi |
| 6,048,623 A | 4/2000 | Everhart et al. |
| 6,060,256 A | 5/2000 | Everhart et al. |
| 6,080,391 A | 6/2000 | Tsuchiya et al. |
| 6,084,683 A | 7/2000 | Bruno et al. |
| 6,087,184 A | 7/2000 | Magginetti et al. |
| 6,099,484 A | 8/2000 | Douglas et al. |
| 6,103,537 A | 8/2000 | Ullman et al. |
| 6,117,090 A | 9/2000 | Caillouette |
| 6,136,549 A | 10/2000 | Feistel |
| 6,136,611 A | 10/2000 | Saaski et al. |
| 6,139,961 A | 10/2000 | Blankenship et al. |
| 6,151,110 A | 11/2000 | Markart |
| 6,165,798 A | 12/2000 | Brooks |
| 6,171,780 B1 | 1/2001 | Pham et al. |
| 6,171,870 B1 | 1/2001 | Freitag |
| 6,174,646 B1 | 1/2001 | Hirai et al. |
| 6,177,281 B1 | 1/2001 | Manita |
| 6,180,288 B1 | 1/2001 | Everhart et al. |
| 6,183,972 B1 | 2/2001 | Kuo et al. |
| 6,184,042 B1 | 2/2001 | Neumann et al. |
| 6,194,220 B1 | 2/2001 | Malick et al. |
| 6,200,820 B1 | 3/2001 | Hansen et al. |
| 6,221,238 B1 | 4/2001 | Grundig et al. |
| 6,221,579 B1 | 4/2001 | Everhart et al. |
| 6,234,974 B1 | 5/2001 | Catt et al. |
| 6,235,241 B1 | 5/2001 | Catt et al. |
| 6,235,471 B1 | 5/2001 | Knapp et al. |
| 6,235,491 B1 | 5/2001 | Connolly |
| 6,241,863 B1 | 6/2001 | Monbouquette |
| 6,242,268 B1 | 6/2001 | Wieder et al. |
| 6,255,066 B1 | 7/2001 | Louderback |
| 6,261,779 B1 | 7/2001 | Barbera-Guillem et al. |
| 6,268,222 B1 | 7/2001 | Chandler et al. |
| 6,270,637 B1 | 8/2001 | Crismore et al. |
| 6,271,040 B1 | 8/2001 | Buechler |
| 6,281,006 B1 | 8/2001 | Heller et al. |
| 6,284,472 B1 | 9/2001 | Wei et al. |
| 6,287,783 B1 | 9/2001 | Maynard et al. |
| 6,287,871 B1 | 9/2001 | Herron et al. |
| 6,294,392 B1 | 9/2001 | Kuhr et al. |
| D450,854 S | 11/2001 | Lipman et al. |
| 6,331,438 B1 | 12/2001 | Aylott et al. |
| 6,348,186 B1 | 2/2002 | Sutton et al. |
| 6,362,011 B1 | 3/2002 | Massey et al. |
| 6,368,873 B1 | 4/2002 | Chang et al. |
| 6,368,875 B1 | 4/2002 | Geisberg |
| 6,391,558 B1 | 5/2002 | Henkens et al. |
| 6,399,295 B1 | 6/2002 | Kaylor et al. |
| 6,399,397 B1 | 6/2002 | Zarling et al. |
| 6,407,492 B1 | 6/2002 | Avnery et al. |
| 6,411,439 B2 | 6/2002 | Nishikawa |
| 6,413,410 B1 | 7/2002 | Hodges et al. |
| 6,436,651 B1 | 8/2002 | Everhart et al. |
| 6,436,722 B1 | 8/2002 | Clark et al. |
| 6,444,423 B1 | 9/2002 | Meade et al. |
| 6,448,091 B1 | 9/2002 | Massey et al. |
| 6,451,607 B1 | 9/2002 | Lawrence et al. |
| 6,455,861 B1 | 9/2002 | Hoyt |
| 6,461,496 B1 | 10/2002 | Feldman et al. |
| 6,468,741 B1 | 10/2002 | Massey et al. |
| 6,472,226 B1 | 10/2002 | Barradine et al. |
| 6,479,146 B1 * | 11/2002 | Caruso et al. ............... 428/403 |
| 6,509,085 B1 | 1/2003 | Kennedy |
| 6,511,814 B1 | 1/2003 | Carpenter |
| 6,556,299 B1 | 4/2003 | Rushbrooke et al. |
| 6,566,508 B2 | 5/2003 | Bentsen et al. |
| 6,582,930 B1 | 6/2003 | Ponomarev et al. |
| 6,585,939 B1 | 7/2003 | Dapprich |
| 6,613,583 B1 | 9/2003 | Richter et al. |
| 6,617,488 B1 | 9/2003 | Springer et al. |
| 6,670,115 B1 | 12/2003 | Zhang |
| 6,787,368 B1 | 9/2004 | Wong et al. |
| 6,815,218 B1 | 11/2004 | Jacobson et al. |
| 7,144,742 B2 | 12/2006 | Boehringer et al. |
| 2002/0070128 A1 | 6/2002 | Beckmann |
| 2002/0101590 A1 | 8/2002 | Shimaoka |
| 2002/0146754 A1 | 10/2002 | Kitawaki et al. |
| 2002/0164659 A1 | 11/2002 | Rao et al. |
| 2003/0017615 A1 | 1/2003 | Sidwell et al. |
| 2003/0178309 A1 | 9/2003 | Huang et al. |
| 2004/0014073 A1 * | 1/2004 | Trau et al. ..................... 435/6 |
| 2004/0197820 A1 * | 10/2004 | Wei et al. ..................... 435/7.1 |

FOREIGN PATENT DOCUMENTS

| | | |
|---|---|---|
| EP | 0469377 A2 | 2/1992 |
| EP | 0539035 A2 | 4/1993 |
| EP | 0539035 B1 | 4/1993 |
| EP | 0617285 A2 | 9/1994 |
| EP | 0617285 A3 | 9/1994 |
| EP | 0657737 A2 | 6/1995 |
| EP | 0657737 A3 | 6/1995 |
| EP | 0703454 A1 | 3/1996 |
| EP | 0711414 B1 | 5/1996 |
| EP | 0745843 A2 | 12/1996 |
| EP | 0745843 A3 | 12/1996 |
| EP | 0833159 A2 | 4/1998 |
| EP | 0859230 A1 | 8/1998 |
| EP | 0898169 B1 | 2/1999 |
| GB | 2273772 A | 6/1994 |
| WO | WO 8804777 A1 | 6/1988 |
| WO | WO 9005305 A1 | 5/1990 |
| WO | WO 9105999 A2 | 5/1991 |
| WO | WO 9221769 A1 | 12/1992 |
| WO | WO 9221770 A1 | 12/1992 |
| WO | WO 9221975 A1 | 12/1992 |
| WO | WO 9301308 A1 | 1/1993 |
| WO | WO 9406012 A1 | 3/1994 |
| WO | WO 9413835 A1 | 6/1994 |
| WO | WO 9415193 A1 | 7/1994 |
| WO | WO 9626435 A1 | 8/1996 |
| WO | WO 9709620 A1 | 3/1997 |
| WO | WO 9737222 A1 | 10/1997 |
| WO | WO 9810334 A1 | 3/1998 |
| WO | WO 9815831 A1 | 4/1998 |
| WO | WO 9827417 A1 | 6/1998 |
| WO | WO 9843086 A1 | 10/1998 |
| WO | WO 9910742 A1 | 3/1999 |
| WO | WO 9930131 A1 | 6/1999 |
| WO | WO 9936777 A1 | 7/1999 |
| WO | WO 9964864 A1 | 12/1999 |

| WO | WO 0019199 A1 | 4/2000 |
| WO | WO 0023805 A1 | 4/2000 |
| WO | WO 0034781 A1 | 6/2000 |
| WO | WO 0036416 A1 | 6/2000 |
| WO | WO 0047983 A1 | 8/2000 |
| WO | WO 0050891 A1 | 8/2000 |
| WO | WO0078917 A1 | 12/2000 |
| WO | WO 0129559 A1 | 4/2001 |
| WO | WO 0138873 A2 | 5/2001 |
| WO | WO 0150129 A2 | 7/2001 |
| WO | WO 0150129 A3 | 7/2001 |
| WO | WO 0163299 A1 | 8/2001 |
| WO | WO 0198765 A1 | 12/2001 |
| WO | WO 0198785 A2 | 12/2001 |
| WO | WO 02077646 A1 | 10/2002 |
| WO | WO 03058246 A1 | 7/2003 |

OTHER PUBLICATIONS

*Flow-Based Microimmunoassay*, Analytical Chemistry, vol. 73, No. 24, Mark A. Hayes, Nolan A. Polson, Allison, N. Phayre, and Antonia A. Garcia, pp. 5896-5902, Dec. 15, 2001.
Article—*How to Build a Spectrofluorometer*, Spex Fluorolog 3, Horiba Group, pp. 1-14.
Article—*Principle and Applications of Size-Exclusion Chromatography*, Impact Analytical, pp. 1-3.
Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.
Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.
Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.
Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.
Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.
Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.
Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.
Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.
Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.
Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.
Article—*Hollow latex particles: synthesis and applications*, Charles J. McDonald and Michael J. Devon, Advances in Colloid and Interface Science, Vo. 99, 2002, pp. 181-213.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.
Article—*Orientation dependence of surface segregation in a dilute Ni-Au alloy*, W . C. Johnson, N. G. Chavka, R. Ku, J. L. Bomback, and P. P. Wynblatt, J. Vac. Sci. Technol. vol. 15, No. 2, Mar./Apr. 1978, pp. 467-469.
Article—*Volume Phase Transition of N-Alkylacrylamide Gels*, S. Saito, M. Konno, and H. Inomata, Advances in Polymer Science, vol. 109, 1992, pp. 207-232.
Article—*Molecular Design Temperature-Responsive Polymers as Intelligent Materials*, Teruo Okano, Advances in Polymer Science, pp. 179-197, 1993.
Article—*Molecular Gradients of w-Substituted Alkanethiols on Gold: Preparation and Characterization*, Bo Liedberg and Pentti Tengvall, Langmuir, vol. 11, No. 10, 1995, pp. 3821-3827.
Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.
Article—*Analysis of electrical equivalent circuit of quartz crystal resonator loaded with viscous conductive liquids*, Journal of Electroanalytical Chemistry, vol. 379, 1994, pp. 21-33.
Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.
Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.
Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.
Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.
Article—*Intelligent Gels*, Yoshihito Osada and Simon B. Ross-Murphy, Scientific American, May 1993, pp. 82-87.
Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.
Article—*On the use of Zx-LiNbO$_3$ acoustic plate mode devices as detectors for dilute electrolytes*, F. Josse, Z. A. Shana, D. T. Haworth, and S. Liew, Sensors and Actuators B, vol. 9, 1992, pp. 92-112.
Article—*Probing of strong and weak electrolytes with acoustic wave fields*, R. Dahint, D. Grunze, F. Josse, and J. C. Andle, Sensors and Actuators B, vol. 9, 1992, pp. 155-162.
Article—*Patterned Condensation Figures as Optical Diffraction Gratings*, Amit Kumar and George M. Whitesides, Science, vol. 263, Jan. 7, 1994, pp. 60-62.
Article—*Stimuli-Responsive Poly(N-isopropylacrylamide) Photo- and Chemical-Induced Phase Transitions*, Advances in Polymer Science, pp. 50-65, 1992.
Article—*Quantitative Prediction of Surface Segregation*, M. P. Seah, Journal of Catalysts, vol. 57, 1979, pp. 450-457.
Article—*Sensing liquid properties with thickness-shear mode resonators*, S. J. Martin, G. C. Frye, and K. O. Wessendorf, Sensors and Actuators A, vol. 44, 1994, pp. 209-218.
Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.
Article—*New Approach to Producing Patterned Biomolecular Assemblies*, Suresh K. Bhatia, James J. Hickman, and Frances S. Ligler, J. Am. Chem. Soc., vol. 114, 1992, pp. 4433-4434.
Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article—*Patterned Functionalization of Gold and Single Crystal Silicon via Photochemical Reaction of Surface-Confined Derivatives of $(n^5$-$C_5H_5)Mn(CO)_3$*, Doris Kang and Mark S. Wrighton, Langmuir, vol. 7, No. 10, 1991, pp. 2169-2174.

Article—*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 2 pages, 1993.

Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages, 1995.

Article—*The Use of Self-Assembled Monolayers and a Selective Etch to Generate Patterned Gold Features*, Amit Kumar, Hans A. Biebuyck, Nicholas L. Abbott, and George M. Whitesides, Journal of the American Chemical Society, vol. 114, 1992, 2 pages.

Article—*Patterned Metal Electrodeposition Using an Alkanethiolate Mask*, T. P. Moffat and H. Yang, J. Electrochem. Soc., vol. 142, No. 11, Nov. 1995, pp. L220-L222.

Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.

Article—*Attempts of Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.

Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.

Article—*Application of rod-like polymers with ionophores as Langmuir-Blodgett membranes for Si-based ion sensors*, Sensors and Actuators B, 1992, pp. 211-216.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Responsive Gels: Volume Transitions I*, M. Ilavský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages, 1993.

*The colloidal state*, Introduction to Colloid and Surface Chemistry, $4^{th}$ Ed., 17 pages, 1992.

*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

*Working With FluoSpheres® Fluorescent Microspheres*, Properties and Modifications, Production Information from Molecular Probes, Mar. 9, 2001, pp. 1-5.

*FluoSpheres® Fluorescent Microspheres*, Production Information from Molecular Probes, Mar. 13, 2001, pp. 1-6.

*Fluorescent Microsphere Standards for Flow Cytometry and Fluorescence Microscopy* from Molecular Probes, pp. 1-8.

*POSS Polymer Systems* from Hybrid Plastics, 3 pages.

*Factors influencing the formation of hollow ceramic microspheres by water extraction of colloidal droplets*, J. Mater. Res., vol. 10, No. 1, p. 84.

*Dualite® Polymeric Microspheres*, from Pierce & Stevens Corp. A subsidiary of Sovereign Specialty Chemicals, Inc., 2 pages.

*ECCOSPHERES® glass microspheres—hollow glass microspheres* from Emerson & Cuming Composite Materials, Inc., 1 page.

*Dynabeads® Biomagnetic Separation Technology—The Principle* from Dynal Biotech, 2 pages.

*CELQUAT® SC-230M (28/6830)*, Polyquaternium-10, from National Starch & Chemical, 1 page.

*CELQUAT® SC-230M (28/6830)*, CELQUAT® SC-240C and SC-230M, from National Starch & Chemical, 1 page.

*Making sun exposure safer for everyone* from Rohm and Haas Company (Bristol Complex), 2 pages.

Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.

Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.

Article —*Latex Immunoassays*, Leigh B. Bangs, Journal of Clinical Immunoassay, vol. 13, No. 3, 1990, pp. 127-131.

8 Photographs of Accu-chek® Blood Glucose Meter.

Pamphlet—The ClearPlan® Easy Fertility Monitor.

Abstract of Japanese Patent No. JP 8062214, Mar. 8, 1996.

Article—*A conductometral biosensor for biosecurity*, Zarini Muhammad-Tahir and Evangelyn C. Alocilja, Biosensors & Bioelectronics, vol. 18, 2003, pp. 813-819.

Article —*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

PCT Search Report for PCT/US03/28628, Mar. 18, 2004.

PCT Search Report for PCT/US02/37653, Apr. 7, 2004.

PCT Search Report for PCT/US03/34543, Apr. 6, 2004.

PCT Search Report for PCT/US03/34544, Apr. 20, 2004.

* cited by examiner

ASSAY DEVICES THAT UTILIZE HOLLOW PARTICLES

RELATED APPLICATIONS

The present application is a divisional application of and claims priority to U.S. patent application Ser. No. 10/406,577, which was filed on Apr. 3, 2003, and is hereby incorporated herein by this reference.

BACKGROUND OF THE INVENTION

Various analytical procedures and devices are commonly employed to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that can be used to determine the presence or concentration of that particular antigen in a biological sample.

In many assay devices, labeled particles are used to signal the presence or absence of the analyte of interest, either visually or though the use of an instrument. For instance, commercial examples of fluorescent carboxylated microspheres are available from Molecular Probes, Inc. under the trade names "FluoSphere" (Red 580/605) and "Transfluo-Sphere" (543/620). Commercial examples of colored carboxylated latex beads are also available from Bang's Laboratory, Inc. Gold particles are also commonly utilized.

Despite some success, conventional particles still possess numerous problems when used in assay devices. For instance, conventional latex beads tend to aggregate with each other, thus requiring that they be refrigerated and kept under continuous agitation until use. This aggregation may lead to poor reliability and reproducibility in the assay device. Further, although gold particles have a relatively lower size distribution and do not tend to aggregate as much as latex beads, they are difficult and expensive to manufacture. Many of the commercially available gold particles are also poor in quality. Moreover, most gold particles have a red color that may not be changed, leading to less flexibility in the assay format and design.

As such, a need currently exists for improved particles for incorporation into an assay device.

SUMMARY OF THE INVENTION

In accordance with one embodiment of the present invention, an assay device (e.g., flow-through assay device, diffraction-based assay device, etc.) is disclosed that comprises a plurality of detectable probes, wherein at least one of the detectable probes contains a particle that defines a hollow interior constituting from about 20% to about 100% of the spatial volume occupied by the particle.

The shape of the particle may generally vary as desired. For example, in some embodiments, the particle may have the shape of a sphere, plate, rod, disc, bar, tube, an irregular shape, etc. In addition, the size of the particle may also vary. For example, in some embodiments, the average size of the particle may range from about 0.1 nanometers to about 1,000 microns, in some embodiments from about 0.1 nanometers to about 100 microns, and in some embodiments, from about 1 nanometer to about 10 microns.

Besides size and/or shape, the material(s) that form the hollow particle may also vary. The hollow particle may, for instance, be organic and/or inorganic in nature, and may be polymers, oligomers, molecules, and so forth. For instance, in one embodiment, the particle is formed from a core polymer and a shell polymer. In another embodiment, the particle is formed by electrostatic layer deposition. The particle may be modified in any manner desired to facilitate its use in the assay device. For example, in some embodiments, the particle is conjugated with a specific binding member. In one embodiment, the specific binding member is covalently bonded to the particle.

In accordance with another embodiment of the present invention, a detectable probe for use in an assay device is disclosed. The detectable probe contains a particle that defines a hollow interior constituting from about 20% to about 100% of the spatial volume occupied by the particle.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes can include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MIB (CK-MB); digoxin; phenyloin; phenobarbitol; carbamazepine; vancomycin; gentamycin; theophylline; valproic acid; quinidine; leutinizing hormone (LH); follicle stimulating hormone (FSH); estradiol, progesterone; C-reactive protein; lipocalins; IgE antibodies; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg);

antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a material suspected of containing the analyte. The test sample can be used directly as obtained from the source or following a pretreatment to modify the character of the sample. The test sample can be derived from any biological source, such as a physiological fluid, including, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The test sample can be pretreated prior to use, such as preparing plasma from blood, diluting viscous fluids, and the like. Methods of treatment can involve filtration, precipitation, dilution, distillation, mixing, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

The present invention is generally directed to the use of hollow particles in various types of assay devices. Generally speaking, the hollow particles individually define a hollow interior that constitutes from about 20% to about 100%, and in some embodiments, from about 30% to about 100% of the spatial volume occupied by the particle. Namely, a substantial portion of the spatial volume of each hollow particle remains empty. Due to their hollow or voided structure, the particles may exhibit a variety of beneficial properties. For instance, hollow particles are generally lightweight, and thus, sometimes inexpensive in comparison to other types of particles. Hollow particles may also form a stable system without requiring refrigeration or rotation, and may be readily resuspended when it is desired to use the particles. In addition, hollow particles may possess enhanced light diffraction capabilities, which may be particularly beneficial in certain types of assay devices, e.g., diffraction-based assay devices.

The shape of the hollow particles may generally vary. In one particular embodiment, for instance, the hollow particles are spherical in shape. However, it should be understood that other shapes are also contemplated by the present invention, such as plates, rods, discs, bars, tubes, irregular shapes, etc.

In addition, the size of the hollow particles may also vary. For instance, the average size (e.g., diameter) of the hollow particles may range from about 0.1 nanometers to about 1,000 microns, in some embodiments, from about 0.1 nanometers to about 100 microns, and in some embodiments, from about 1 nanometer to about 10 microns. The size selected for the hollow microparticles may depend on the intended application. For instance, "micron-scale" particles may be desired in some assay devices, such as some flow-through devices or diffraction-based assays. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may be desired in other applications, such as in some flow-through assay devices. When utilized, such "nano-scale" particles may have an average size of from about 0.1 to about 10 nanometers, in some embodiments from about 0.1 to about 5 nanometers, and in some embodiments, from about 1 to about 5 nanometers.

Although the shape and size of the particles may vary, as described above, it is often desired that the particles may be relatively "monodispersed" in that the particles within a given dispersion have approximately the same size and/or shape. Monodispersed hollow particles can provide improved reliability and reproducibility due to their generally uniform properties.

Besides their size and shape, the material(s) that form the hollow particles may also vary. The hollow particles may, for instance, be organic and/or inorganic in nature, and may be polymers, oligomers, molecules, and so forth. For example, the hollow particles may be formed from polymers such as polystyrene, (meth)acrylate polymers or copolymers, vinylidene chloride/acrylonitrile copolymers, etc. Other suitable hollow polymeric particles may be described in U.S. Pat. No. 4,427,836 to Kowalski, et al.; U.S. Pat. No. 4,480,042 to Craig, et al.; U.S. Pat. No. 4,973,670 to McDonald, et al.; U.S. Pat. No. 5,618,888 to Choi, et al.; and U.S. Pat. No. 6,139,961 to Blankenship, et al., which are incorporated herein in their entirety by reference thereto for all purposes. Still other hollow particles that may be used include inorganic materials, such as glass hollow particles. For instance, ECCO-SPHERES® are hollow glass particles derived from sodium borosilicate commercially available from Emerson and Cuming Composite Materials, Inc. Other representative hollow particles derived from an inorganic material, include, for instance, silica hollow microspheres available under the trade name "SILICA BEADS S700" from Miyoshi Kasei, Inc. Other examples of hollow inorganic particles are described in U.S. Pat. No. 6,416,774 to Radin, et al., which is incorporated herein in its entirety by reference thereto for all purposes.

In one particular, embodiment, the hollow particles may be formed from one or more natural or synthetic latex polymers. Examples of such latex-based hollow particles are described in U.S. Pat. No. 5,663,213 to Jones, et al., which is incorporated herein in its entirety by reference thereto for all purposes, and commercially available from Rohm & Haas of Philadelphia, Pa. under the name SunSpheres®. The '213 patent describes the ability of such latex-based hollow particles, which are typically "micron-scale" in size, to be used for sun protection. However, the present inventors have also discovered that the latex-based hollow particles have unexpected utility in assay devices.

The latex-based hollow particles are typically formed from a core polymer and a shell polymer. The monomers used to form the core and shell polymers may generally vary. For instance, the shell polymer may be selected to provide a glass transition temperature ($T_g$) that is high enough to support the voids of the particle, e.g., such as greater than about 50° C., in some embodiments greater than about 60° C., and in some embodiments, greater than about 70° C. Some examples of suitable monomers that may be used to form the shell polymer include, but are not limited to, non-ionic ethylenically unsaturated monomers, monoethylenically unsaturated monomers containing at least one carboxylic acid group, and so forth.

The monomers that form the core polymer may include one or more monoethylenically unsaturated monomers containing at least one carboxylic acid group. In some embodiments, for instance, at least about 5 wt. % of the monoethylenically unsaturated monomers of the core polymer contain at least one carboxylic acid, based on total monomer weight of the core. Examples of suitable monoethylenically unsaturated monomers containing at least one carboxylic acid group include, but are not limited to, (meth)acrylic acid, acryloxypropionic acid, (meth)acryloxypropionic acid, itaconic acid, aconitic acid, maleic acid or anhydride, fumaric acid, crotonic acid, monomethyl maleate, monomethyl fumarate, monomethyl itaconate, and so forth. As used herein, the term "(meth) acrylic" is intended to serve as a generic expression embracing both acrylic and methacrylic.

In one embodiment, the monoethylenically unsaturated monomer containing at least on, e carboxylic acid group is copolymerized with one or more nonionic (e.g., having no ionizable group) ethylenically unsaturated monomers. Some suitable nonionic ethylenically unsaturated monomers include, but are not limited to, styrene, vinyltoluene, ethylene, vinyl acetate, vinyl chloride, vinylidene chloride, acrylonitrile, (meth)acrylamide, ($C_1$-$C_{20}$) alkyl or ($C_3$-$C_{20}$) alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate, stearyl (meth)acrylate, and so forth.

The core polymer and/or shell polymer may optionally contain from about 0.1 wt. % to about 20 wt. %, and in some embodiments, from about 0.1 wt. % to about 3 wt. % of a polyethylenically unsaturated monomer based on the total monomer weight of the polymer. Examples of such unsaturated monomers include, but are not limited to, ethylene glycol di(meth)acrylate, allyl(meth)acrylate, 1,3-butanediol di(meth)acrylate, diethylene glycol di(meth)acrylate, trimethylolpropane tri(meth)acrylate, or divinylbenzene. If desired, the core polymer and/or shell polymer may contain from about 0.1 wt. % to about 60 wt. % butadiene based on the total monomer weight of the polymer.

To produce the void in the latex particles, the core is typically swelled with a swelling agent containing one or more volatile components. The swelling agent permeates the shell to swell the core. The volatile components of the swelling agent may then be removed by drying the latex particles, thereby causing a void to form within the latex particles. Although not required, the swelling agent may be an aqueous base. Examples of suitable aqueous bases include, but are not limited to, ammonia, ammonium hydroxide, alkali metal hydroxides, such as sodium hydroxide, or a volatile amine, such as trimethylamine or triethylamine. Removal of the templated core may also be accomplished in other ways, such as by calcining at elevated temperatures or by chemical reactions causing dissolution of the core material.

In addition to core-shell hollow particles, hollow particles may also be formed using other well-known techniques. For example, U.S. Pat. No. 6,479,146 to Caruso, et al., which is incorporated herein in its entirety by reference thereto for all purposes, describes hollow particles formed using electrostatic forces. In particular, hollow particles are formed using colloid templated electrostatic layer-by-layer ("LBL") self-assembly of nanoparticle-polymer multilayers, followed by removal of the templated core. The template particles may, for instance, contain organic polymer latices, such as polystyrene or styrene copolymer latices.

The template particles are alternately coated with polyelectrolyte molecules and nanoparticles. The polyelectrolytes are usually polymers having ionically dissociable groups that may be a component or substituent of the polymer chain. The nanoparticles are typically ceramic particles, such as silicon dioxide, titanium dioxide, and zirconium dioxide optionally doped with other metal oxides; magnetic particles, such as $Fe_3O_4$; magneto-optical particles; nitridic ceramic particles, such as $Si_3N_4$, carbidic ceramic particles; metallic particles, such as gold, silver, and palladium; and sulfur or selene-containing particles, such as cadmium sulfide, cadmium selenide etc.

In one embodiment, the template particles are first coated with several layers of oppositely charged cationic and anionic polyelectrolytes before the alternating layers of nanoparticles and polyelectrolyte or the alternating nanoparticle layers are applied. The template particles may be coated with at least two and up to six layers of oppositely charged cationic and anionic polyelectrolytes, e.g., with three layers. The outermost polyelectrolyte layer may be oppositely charged with regard to the nanoparticle to be deposited. In most embodiments, the template particles are at least partially disintegrated after the coating has been completed. They can be dissolved in appropriate solvents or thermally (e.g., by calcination to temperatures of at least about 500° C.). After dissolution of the template particles, hollow shells remain that are composed of the nanoparticle material and optionally the polyelectrolyte material.

If desired, the electrostatically-formed particles may be modified to contain pores in at least one of the layers. Such pores can be formed by the polyelectrolytes or nanoparticles themselves. For instance, a high salt concentration of the medium used for the deposition of the polyelectrolyte may result in a high permeability of the shell wall. On the other hand, a high salt concentration of the medium used for the deposition of the nanoparticles (e.g., $SiO_2$) may results in a high packing density of the silica particles. Thus, by adjusting the salt concentrations in the deposition medium, the permeability of the shell can be controlled, as desired. Further, the permeability properties of the shell may be modified by selecting the conditions for decomposing the core, e.g., by selecting the temperature and heating conditions in a calcination procedure.

Hollow particles, such as described above, may have a variety of uses in assay devices. For instance, in one particular embodiment, the hollow particles may be used as probes in an assay device. When utilized as probes, the hollow particles may be capable of inherently generating a signal that is detectable visually or by an instrumental device (e.g., a diffraction pattern), or may be modified with a label to impart such a signal generation capability. Various suitable labels that can be used include, but are not limited to, chromogens;

catalysts; fluorescent compounds; chemiluminescent compounds; phosphorescent compounds; radioactive compounds; direct visual labels; and the like. For instance, some suitable labels may be described in U.S. Pat. No. 5,670,381 to Jou, et al. and U.S. Pat. No. 5,252,459 to Tarcha, et al., which are incorporated herein in their entirety by reference thereto for all purposes. In one particular embodiment, the label is a fluorescent compound that produces a detectable signal. The fluorescent compounds can be fluorescent molecules, polymers, dendrimers, particles, and the like. Some examples of suitable fluorescent molecules, for instance, include, but are not limited to, fluorescein, europium chelates, phycobiliprotein, rhodamine and their derivatives and analogs. A visually detectable, colored compound can also be used as a label, thereby providing for a direct colored readout of the presence or concentration of the analyte in the sample without the need for further signal producing reagents.

The hollow particles may also be modified in some manner so that they are more readily able to bond with an analyte. In such instances, the hollow particles can be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members can include antigens, haptens, aptamers, antibodies, and complexes thereof, including those formed by recombinant DNA methods or peptide synthesis. An antibody can be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin, biotin and streptavidin, antibody-binding proteins (such as protein A or G) and antibodies, carbohydrates and lectins, complementary nucleotide sequences (including label and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

Figure 3:
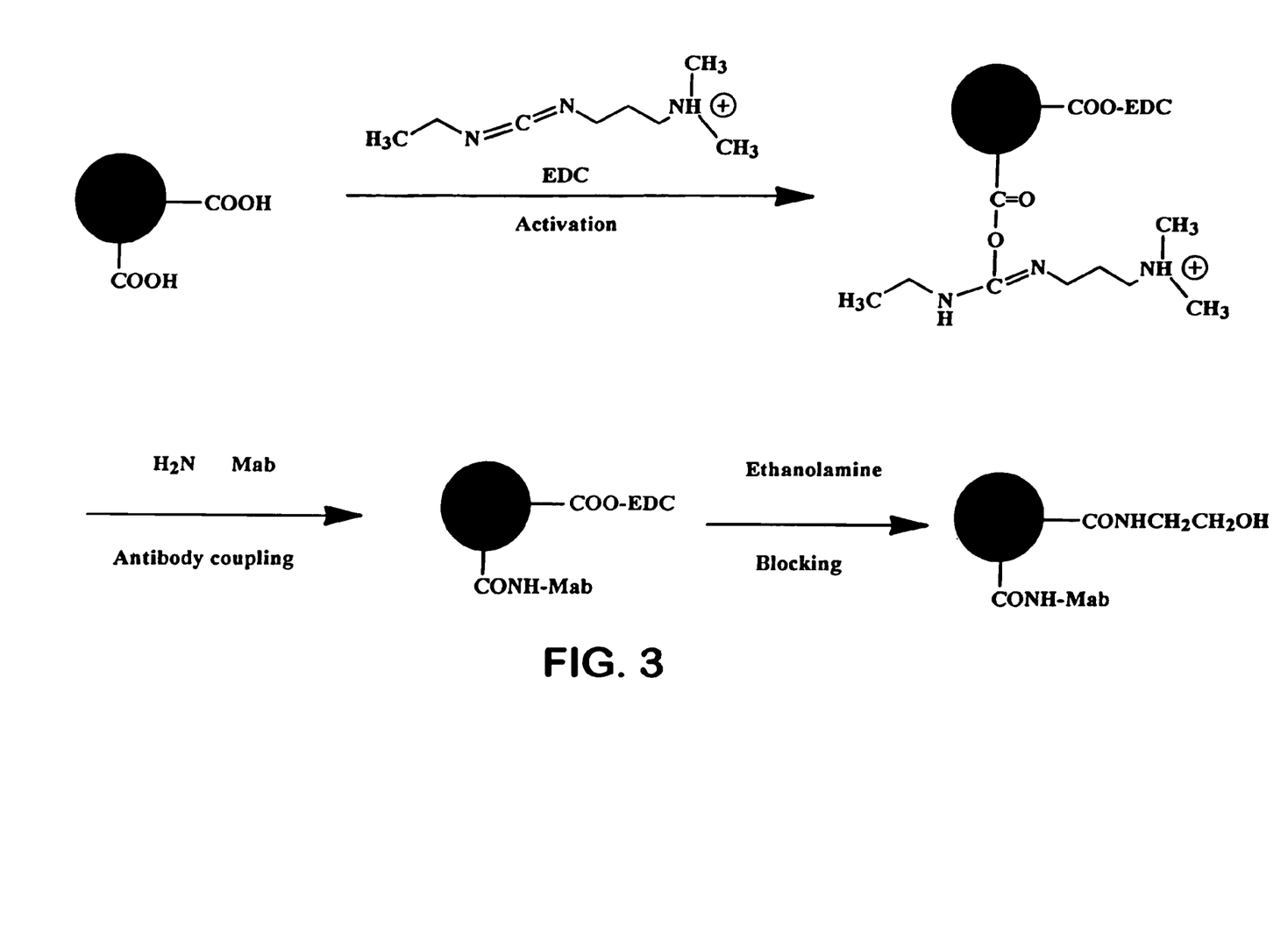
FIG. 3 is a graphical illustration of one embodiment for covalently conjugating an antibody to carboxylated hollow particles.

The specific binding members can generally be attached to the hollow particles using any of a variety of well-known techniques. For instance, covalent attachment of the specific binding members to the hollow particles can be accomplished using carboxylic, amino, aldehyde, bromoacetyl, iodoacetyl, thiol, epoxy and other reactive or linking functional groups, as well as residual free radicals and radical cations, through which a protein coupling reaction can be accomplished. A surface functional group can also be incorporated as a functionalized co-monomer because the surface of the hollow particles can contain a relatively high surface concentration of polar groups. In addition, although the hollow probes are often functionalized after synthesis, in certain cases, the hollow particles may be capable of direct covalent linking with a protein without the need for further modification. For example, referring to FIG. 3, one embodiment of the present invention for covalently conjugating a hollow particle is illustrated. In this embodiment, the hollow particles contain carboxylic functional groups, which may be present on latex-based hollow particles, such as described above. As shown, the first step of conjugation is activation of carboxylic groups on the hollow particle surface using carbodiimide. In the second step, the activated carboxylic acid groups are reacted with an amino group of an antibody to form an amide bond. The activation and/or antibody coupling can occur in a buffer, such as phosphate-buffered saline (PBS) (e.g., pH of 7.2) or 2-(N-morpholino) ethane sulfonic acid (MES) (e.g., pH of 5.3). As shown, the resulting hollow particles can then be blocked with ethanolamine, for instance, to block any remaining activated sites. Overall, this process forms a conjugate, where the antibody is covalently attached to the particle. Besides covalent bonding, other attachment techniques, such as physical adsorption, may also be utilized in the present invention.

Hollow particles, such as described above, may be incorporated into a variety of assay devices. Examples of some suitable assay devices that may employ the hollow particles include, but are not limited to, flow through-assay devices (membrane-based, fluidic-based, capillary-based, etc.); diffraction-based assay devices; and so forth. Specifically, such assay devices often utilize probes that are detectable in some manner, such as visually or through the use of an instrument. Such detectable probes may be used for detecting the analyte and/or for calibration of the assay device. In accordance with the present invention, the hollow particles may be utilized as detectable probes for purposes of detection and/or calibration. Of course, it should also be understood that the hollow particles may be used in an assay device according to the present invention in other ways not specifically referenced herein.

For purposes of illustration only, various examples of assay devices that may incorporate hollow particles according to the present invention will now be described in more detail. It should be understood, however, that other assay devices are also contemplated by the present invention. In fact, the present invention is not limited to any particular assay device configuration.

Figure 1:
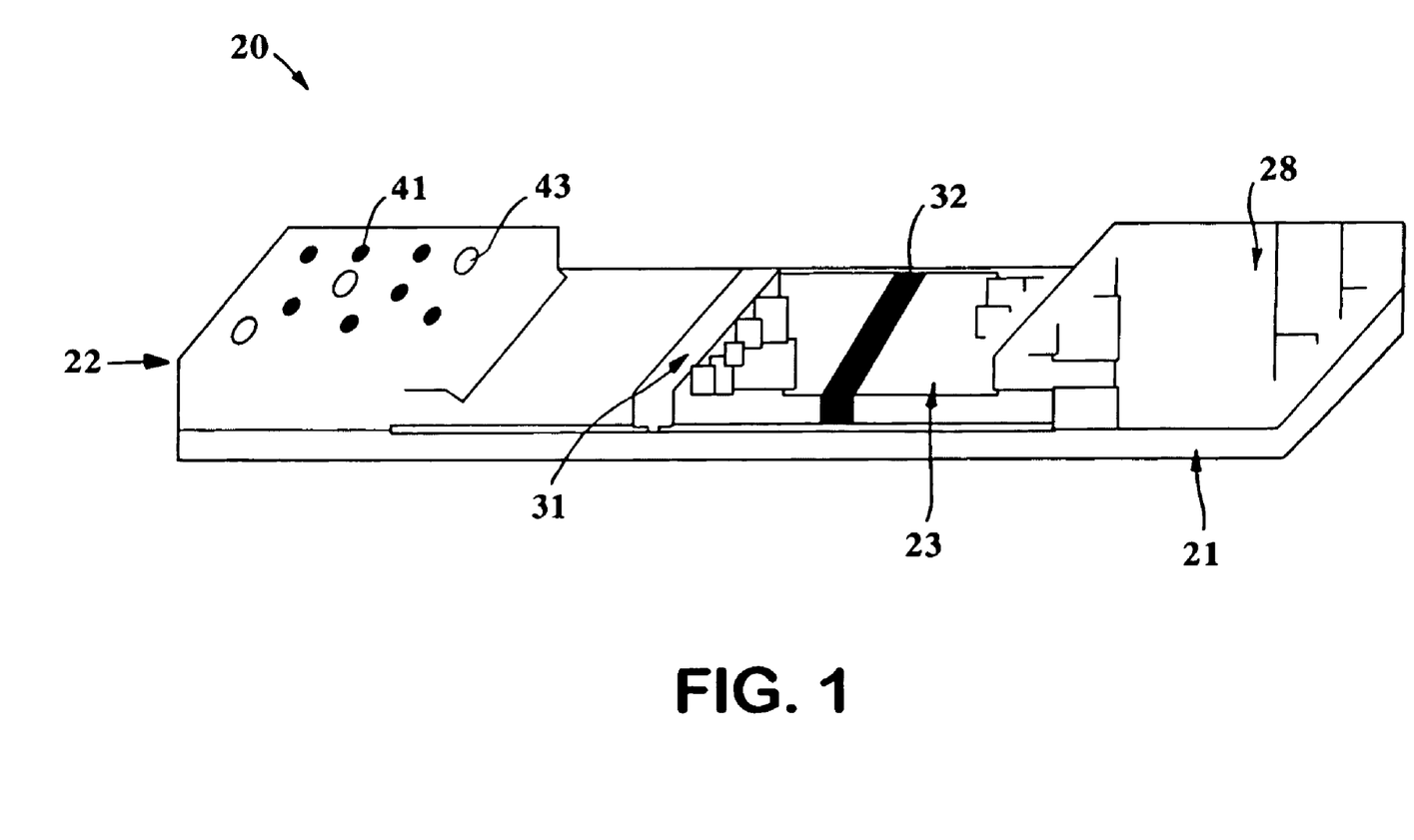
FIG. 1 is a perspective view of one embodiment of a flow-through assay device of the present invention.

Referring to FIG. 1, for instance, one embodiment of a membrane-based flow-through assay device 20 is illustrated. As shown, the device 20 contains a porous membrane 23 optionally supported by a rigid material 21. In general, the porous membrane 23 can be made from any of a variety of materials through which the test sample is capable of passing. For example, the materials used to form the porous membrane 23 can include, but are not limited to, natural, synthetic, or naturally occurring materials that are synthetically modified, such as polysaccharides (e.g., cellulose materials such as paper and cellulose derivatives, such as cellulose acetate and nitrocellulose); silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 can assist in promoting capillary action and fluid flow through the membrane 23.

To initiate the detection of an analyte within the test sample, a user may directly apply the test sample to a portion of the porous membrane 23 through which it can then travel. Alternatively, the test sample may first be applied to a sampling pad (not shown) that is in fluid communication with the porous membrane 23. Some suitable materials that can be used to form the sampling pad include, but are not limited to, nitrocellulose, cellulose, porous polyethylene pads, and glass fiber filter paper. If desired, the sampling pad may also contain one or more assay pretreatment reagents, either diffusively or non-diffusively attached thereto.

In the illustrated embodiment, the test sample travels from the sampling pad (not shown) to a conjugate pad 22 that is placed in communication with one end of the sampling pad. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate detection of the presence or absence of an analyte within the test sample, various detection probes 41, which optionally contain the hollow particles of the present invention, may be applied to the conjugate pad 22. While contained on the conjugate pad 22, these detection probes 41 remain available for binding with the analyte as it passes from the sampling pad through the conjugate pad 22. Upon binding with the analyte, the detection probes 41 can later serve to identify the presence or absence of the analyte. The detection probes 41 may be used for both detection and calibration of the device 20. In alternative embodiments, however, separate calibration probes 43, which also optionally contain the hollow particles of the present invention, may be applied to the conjugate pad 22 for use in conjunction with the detection probes 41 to facilitate simultaneous calibration and detection, thereby eliminating inaccuracies often created by conventional assay calibration systems. It should be understood, however, that the detection probes 41 and/or the calibration probes 43 may be applied together or separately at any location of the device 20, and need not be applied to the conjugate pad 22. Further, it should also be understood that the detection probes 41 and/or the calibration probes 43 may be applied to the same or different conjugate pads.

In one embodiment, for instance, the test sample travels to the conjugate pad 22, where the analyte mixes with the detection probes 41 to form analyte complexes. Because the conjugate pad 22 is in fluid communication with the porous membrane 23, the complexes can migrate from the conjugate pad 22 to a detection zone 31 present on the porous membrane 23. The detection zone 31 may contain an immobilized receptive material that is generally capable of forming a chemical or physical bond with the probes. For example, in some embodiments, the binders can contain a biological receptive material. For example, in some embodiments, the receptive material may be a biological receptive material. Such biological receptive materials are well known in the art and can include, but are not limited to, antigens, haptens, antibodies, protein A or G, avidin, streptavidin, secondary antibodies, and complexes thereof. In some cases, it is desired that these biological receptive materials are capable of binding to a specific binding member (e.g., antibody) present on the hollow particles. In addition, it may also be desired to utilize various non-biological materials for the receptive material. For instance, in some embodiments, the receptive material can include a polyelectrolyte that can bind to the uncaptured probes. The polyelectrolytes can have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and the like. In one particular embodiment, CelQuat® SC-230M or H-100 (available from National Starch & Chemical, Inc.), which are cellulosic derivatives containing a quaternary ammonium water-soluble monomer, can be utilized. Moreover, some suitable examples of polyelectrolytes having a net negative charge include, but are not limited to, polyacrylic acids, such as poly(ethylene-co-methacrylic acid, sodium salt), and the like. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

These receptive materials serve as stationary binding sites for the detection probe/analyte complexes. In some instances, the analytes, such as antibodies, antigens, etc., have two binding sites. Upon reaching the detection zone 31, one of these binding sites is occupied by the specific binding member of the complexed probes. However, the free binding site of the analyte can bind to the immobilized receptive material. Upon being bound to the immobilized receptive material, the complexed probes form a new ternary sandwich complex.

The detection zone 31 may generally provide any number of distinct detection regions so that a user can better determine the concentration of a particular analyte within a test sample. Each region may contain the same receptive materials, or may contain different receptive materials for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions can be disposed in the form of lines in a direction that is substantially parallel to the flow of the test sample through the assay device.

Although the detection zone 31 may indicate the presence of an analyte, it is often difficult to determine the relative concentration of the analyte within the test sample using solely a detection zone 31. Thus, the assay device 20 may also include a calibration zone 32. In this embodiment, the calibration zone 32 is formed on the porous membrane 23 and is positioned downstream from the detection zone 31. The calibration zone 32 is provided with a receptive material that is capable of binding to any remaining uncaptured detection probes 41 and/or calibration probes 43 that pass through the length of the membrane 23. In particular, upon being contacted with the test sample, any uncaptured probes that do not bind to the analyte migrate through the detection zone 31 and enter the calibration zone 32 of the porous membrane 23. At the calibration zone 32, these uncaptured probes then bind to the receptive materials. The receptive materials utilized in the calibration zone 32 may be the same or different than the receptive materials used in the detection zone 31. Moreover, similar to the detection zone 31, the calibration zone 32 may also provide any number of distinct calibration regions in any direction so that a user can better determine the concentration of a particular analyte within a test sample. Each region may contain the same receptive materials, or may contain different receptive materials for capturing different probes.

The calibration regions may be pre-loaded on the porous membrane 23 with different amounts of the binder so that a different signal intensity is generated by each calibration region upon migration of the uncaptured probes. The overall amount of receptive material within each calibration region can be varied by utilizing calibration regions of different sizes and/or by varying the concentration or volume of the binder in each calibration region. If desired, an excess of probe molecules can be employed in the assay device 20 so that each calibration region reaches its full and predetermined potential for signal intensity. That is, the amount of uncaptured probes that are deposited upon calibration regions are predetermined because the amount of the binder employed on the calibration regions is set at a predetermined and known level. Once captured, the signal of the probes at the detection and calibration zones 31 and 32 can be measured using visually and/or with an instrument.

Various formats may be used to test for the presence or absence of an analyte using the device 20. For instance, in the embodiment described above, a "sandwich" format is utilized. Other examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes. In addition, other formats, such as "competitive" formats, may also be utilized. In a competitive assay, the labeled probe is generally conjugated with an antibody that is identical to, or an analogue of, the analyte. Thus, the labeled antibody competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Besides flow-through assay devices, the hollow particles of the present invention, as mentioned above, may also be utilized in diffraction-based assay devices (i.e., biosensors). The term "diffraction" refers to the phenomenon observed when waves are obstructed by obstacles caused by the disturbance spreading beyond the limits of the geometrical shadow of the object. The effect is marked when the size of the object is of the same order as the wavelength of the waves. For diffraction-based assay devices, the obstacles are analytes (with or without attached particles) and the waves are light waves. For example, various examples of diffraction-based assay devices are described in U.S. Pat. No. 6,221,579 to Everhart, et al., which is incorporated herein in its entirety by reference thereto for all purposes.

Figure 2:
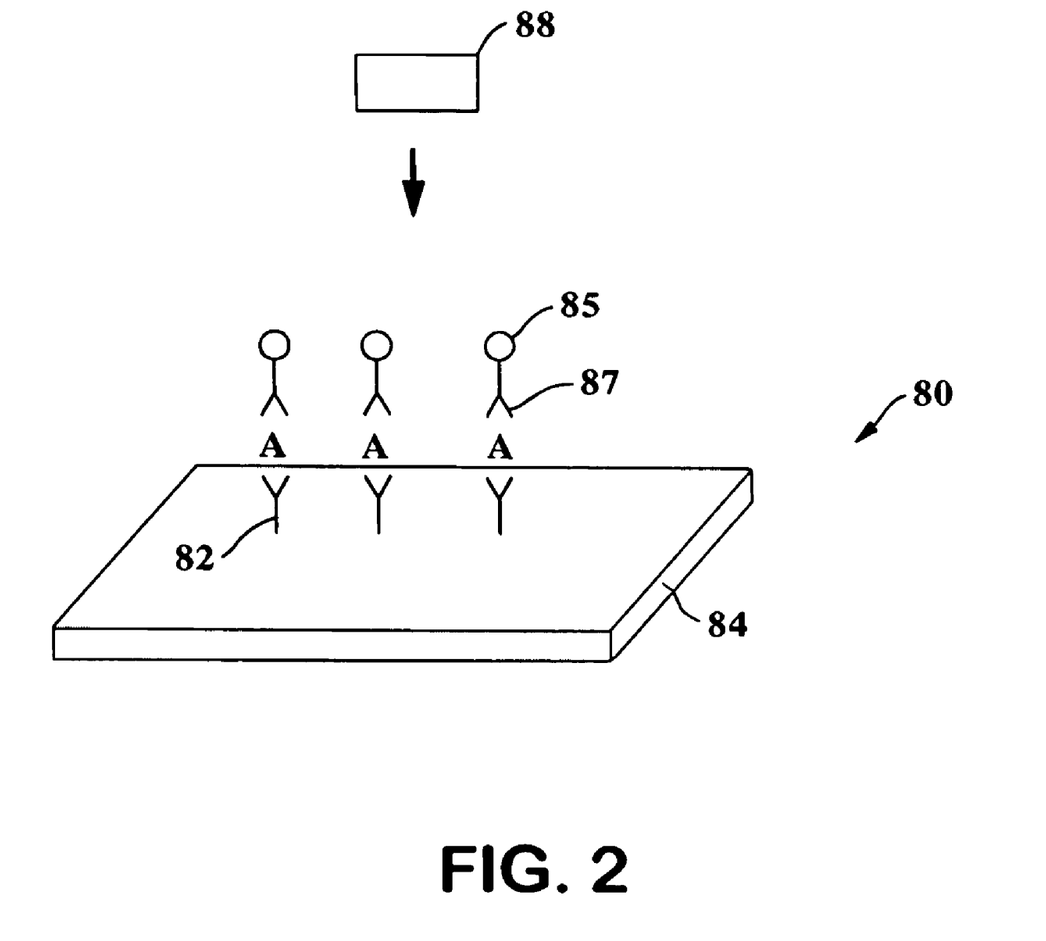
FIG. 2 is a perspective view of one embodiment of a diffraction-based assay device of the present invention.

Referring to FIG. 2, for instance, one embodiment of a diffraction-based assay device 80 is shown in which a receptive material 82, such as described above, is coated onto the surface of a substrate 84. Any one of a wide variety of materials may serve as the substrate 84 to which the receptive material 82 is applied. Such materials are well known to those skilled in the art. For example, the substrate 84 may be formed of any one of a number of suitable plastics, metal coated plastics and glass, functionalized plastics and glass, silicon wafers, foils, glass, etc. Rather than requiring a rigid substrate for the photopatterning process described herein, it has been found that thermoplastic films are quite suitable. Such films include, but are not limited to, polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) poly-ethylene-nylon copolymers, polypropylene, methyl pentene polymers, polyvinyl fluoride, and aromatic polysulfones. Typically, the plastic film has an optical transparency of greater than about 80%. Other suitable thermoplastics and suppliers may be found, for example, in reference works such as the Modern Plastics Encyclopedia (McGraw-Hill Publishing Co., New York 1923-1996).

If desired, the thermoplastic film may have a metal coating. The film with metal coating thereon may have an optical transparency of from about 5% to about 95%. A more desired optical transparency for the thermoplastic film used in the present invention is from about 20% to about 80%. In one embodiment, the thermoplastic film has at least about 80% optical transparency, and the thickness of the metal coating is such as to maintain an optical transparency greater than about 20%, so that diffraction patterns can be produced by either reflected or transmitted light. This corresponds to a metal coating thickness of about 10 to about 20 nanometers. However, in other embodiments, the metal thickness may be between approximately 1 nanometer and 1000 nanometers. The preferred metal for deposition on the film is gold. However, silver, aluminum, chromium, copper, iron, zirconium, platinum, titanium, and nickel, as well as oxides of these metals, may be used. Chromium oxide can be used to make metallized layers.

The receptive material 82 may be applied to the substrate 84 by any conventional method. The receptive material 82 is applied so that it generally uniformly covers an entire (for example, upper) surface of the substrate 84. Although not required, non-contact methods for applying the receptive material 82 may be desired so as to eliminate the possibility of contamination by contact during application. Suitable application methods include, but are not limited to, dipping, spraying, rolling, spin coating, and any other technique wherein the receptive material layer can be applied generally uniformly over the entire test surface of the substrate. Simple physisorption can occur on many materials, such as polystyrene, glass, nylon, or other materials well known to those skilled in the art. One particular embodiment of immobilizing the receptive material layer 82 involves molecular attachment, such as that possible between thiol or disulfide-containing compounds and gold. Typically, a gold coating of about 5 to about 2000 nanometers thick is supported on a silicon wafer, glass, or polymer film (such as a MYLAR® film). The receptive material 82 attaches to the gold surface upon exposure to a solution thereof.

The receptive material layer 82 may also be formed on the substrate 84 as a self-assembling monolayers of alkanethiolates, carboxylic acids, hydroxamic acids, and phosphonic acids on metallized thermoplastic films. The self-assembling monolayers have the receptive material bound thereto. For instance, U.S. Pat. No. 5,922,550, which is incorporated herein in its entirety by reference thereto for all purposes, provides a more detailed description of such self-assembling monolayers and methods for producing the monolayers.

Once the receptive material layer 82 is applied to the substrate 84, a mask (not shown) is then placed over the substrate 84, and the mask and substrate 84 combination is irradiated with an energy source 88. In its basic form, the "mask" serves to shield or "protect" at least one area or section of the receptive material 82 from the irradiating energy source and to expose at least one adjacent section to the energy source 88. For example, the mask may be a generally transparent or translucent blank (e.g., a strip of material) having any pattern of shielded regions printed or otherwise defined thereon. The exposed unshielded regions of the mask correspond to the exposed areas of the substrate 84. Alternatively, the mask may simply be a single object placed upon the substrate 84. The area under the object would be protected and thus define an active area of the receptive material 82, and the area around the object would be exposed to the energy source 88 and thus define an area of inactive receptive material. Alternatively, the object may have any pattern of openings defined therethrough corresponding to the exposed areas.

The mask may be formed of any suitable material that protects the underlying portion of the substrate 84 from the irradiating energy source. A material that has proven useful for defining patterns of active and inactive receptive material regions on a gold-plated MYLAR® film coated with an antibody solution where the energy source is UV light is a transparent or translucent polymer film (such as MYLAR®) having a pattern of shielded or protected regions printed thereon. This type of mask is useful for light sources with a wavelength equal or greater than about 330 nanometers. For light sources having a wavelength below about 330 nanometers, a quartz or fused silica mask having chrome or other metal plated shielded regions defined thereon may be used. It may be desired to select a hole pattern and size so as to maximize the visible diffraction contrast between the active and inactive regions. As one example of a pattern, it has been found suitable if the active regions are defined as generally circular with a diameter of about 10 microns and spaced from each other by about 5 microns. However, other patterns that provide a defined diffraction image would be suitable.

The energy source 88 is selected so that the receptive material 82 exposed by the mask is rendered inactive or incapable of binding analyte. Without being limited by theory, it is believed that one likely mechanism is that the energy source 88 essentially destroys the bond structure of the receptive material 82 by a radical mechanism. The energy source 88 is selected so that the receptive material 82 exposed by the mask is rendered inactive. The energy source 88 essentially destroys the bond structure of the receptive material 82 by a radical mechanism. The receptive material 82 under the shielded areas of the mask is protected during the irradiation step. Thus, upon removal of the mask, a pattern of active and inactive receptive material areas are defined. It should be understood that the term "pattern" includes as few as one active area and one inactive area. Upon subsequent exposure of the diffraction-based assay device to a medium containing the analyte of interest, such analyte will bind to the receptive material in the active areas. The analyte results in diffraction of transmitted and/or reflected light in a visible diffraction pattern corresponding to the active areas.

Any suitable energy source 88 may be selected for irradiating the mask and substrate combination. The energy source 88 may be, for example, a light source, e.g., an ultraviolet (UV) light source, an electron beam, a radiation source, etc. In one particular embodiment, the receptive material 82 is a protein-based material, such as an antibody, and the deactivating energy source 88 is a UV light source. The sensor would be exposed to the UV source for a period of time sufficient for deactivating the antibody. Wavelengths and exposure times may vary depending on the particular type of receptive material. Other suitable energy sources may include tuned lasers, electron beams, various types of radiation beams including gamma and X-ray sources, various intensities and wavelengths of light including light beams of sufficient magnitude at the microwave and below wavelengths, etc. It should be appreciated that any number of energy sources may be specifically tailored for deactivating a particular antibody or other type of biomolecule. Care should be taken that the energy source does not damage (e.g., melt) the underlying substrate or mask.

In some embodiments, the hollow particles of the present invention may be used in a diffraction-based assay device, such as described above, to enhance and/or cause the desired diffraction pattern, particularly if the analyte is not of a size that results in the desired diffraction pattern. For instance, one embodiment includes conjugating hollow particles 85 with specific binding members 87, such as antibodies, that specifically bind to an analyte A. For detecting the analyte A in a test sample, the test sample is first exposed to the hollow particles 85 having the specific binding members 87 thereon. The analyte A will bind to the specific binding members 87. Then, the hollow particles 85 are optionally washed and exposed to the biosensor film 84 with the pattern of active receptive material 82. The receptive material 82 then binds to the analyte A on the hollow particles 85, thereby immobilizing the hollow particles 85 in the same pattern as the active receptive material 82 on the film 84. Because the bound hollow particles 85 will cause diffraction of the visible light, a diffraction pattern is formed, indicating the presence of the analyte A.

Various other diffraction-based assay device configurations may be utilized with hollow particles in accordance with the present invention. For instance, in one embodiment, the test sample may be applied to the assay device simultaneously with the hollow particles. Likewise, in another embodiment, the hollow particles may be first pre-dried on the assay device, and thereafter, the test sample is applied thereto.

Regardless of the specific configuration of the assay device, the hollow particles of the present invention may impart a variety of beneficial characteristics thereto. For instance, one benefit is that many hollow particles, such as hollow latex polymers, form a relatively stable dispersion without the requirement of refrigeration and continual agitation. This can lessen the cost and time required for preparing the assay device and dramatically reduce particle aggregation during conjugation with specific binding members. The particles may also be more readily resuspended for use in the assay device. This is of particular advantage when the hollow particles are pre-dried onto an assay device. In addition, the hollow nature of the particles may allow them to be more "monodispersed", i.e., a dispersion of particles of approximately the same shape and/or size, than conventional latex beads used in assay devices. This can provide improved reliability and reproducibility due to their generally uniform properties. Moreover, because the particles are hollow, they tend to have a lower weight than most conventional beads. The lighter weight hollow particles can move more readily through the assay device, thereby shortening the measurement time of the device. The hollowness of the particles also results in a relatively high refraction index, which can enhance the signal (e.g., diffraction pattern) provided by the particles in some types of assay devices. The refractive index may be especially enhanced in the case where the hollow particles are formed from materials with a high refractive index, such as titanium dioxide or gold. This enhancement may provide a corresponding enhancement in diffraction intensity.

The present invention may be better understood with reference to the following examples.

Example 1

Figure 4:
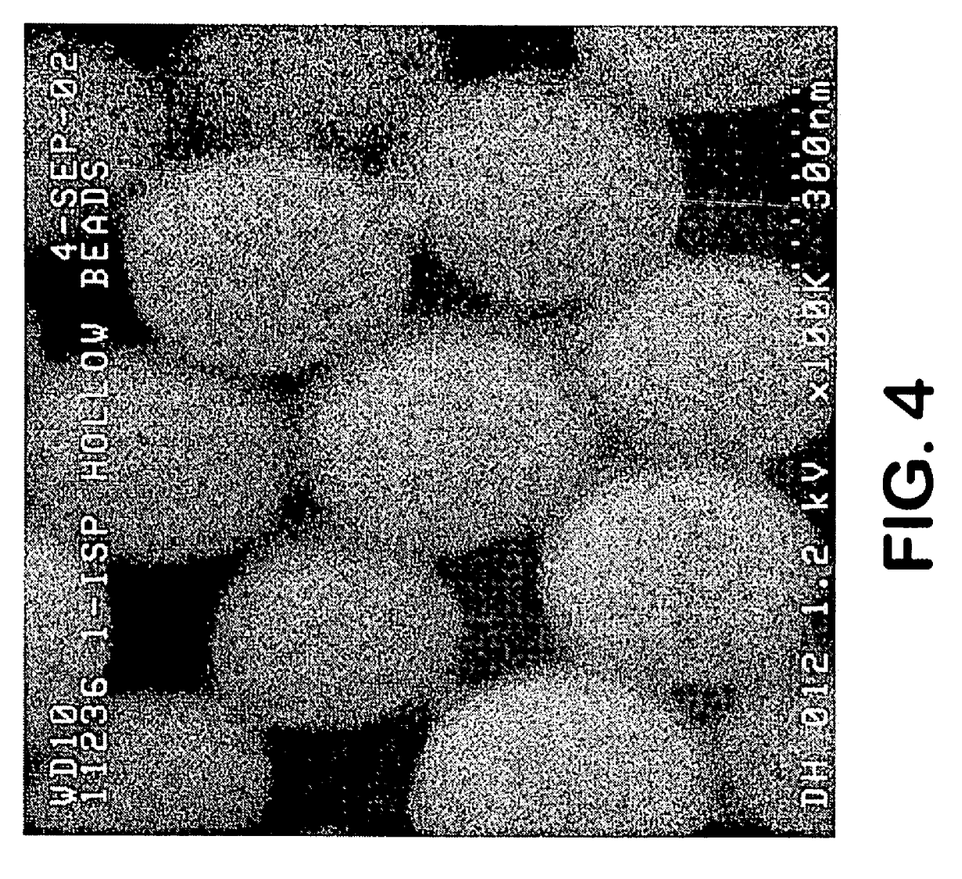
FIG. 4 is an SEM photograph (magnification of 100×) of the hollow particles utilized in Example 1.

The ability to conjugate antibodies onto hollow particles in accordance with the present invention was demonstrated. Initially SunSphere™ hollow particles (available from Rohm & Haas) were provided. The particles had an approximate solids content of 26% and an average measured size of 300 nanometers (based on SEM and particle sizer). An SEM photograph of such hollow particles is shown in FIG. 4.

To begin the conjugation process, 50 microliters of the hollow particles were placed in an Eppendorf microcentrifuge tube (1.5 to 1.9 milliliter capacity). A carbonate buffer was added to fill the tube and the cap closed. The contents of the tube were centrifuged for 6 minutes on high setting (recommended=12,000 rpms). After centrifuging, the supernatant was removed using a pipette and discarded. The resulting pellet was resuspended in a phosphate buffer by filling one half of the tube and vortexing the pellet until completely dispersed. The tube was then filled to capacity and centrifuged for 6 minutes at 12000 rpms. The supernatant was again removed and discarded, and the remaining pellet resuspended, and sonicated.

0.75 milliliters of a 2% carbodiimide solution was then made by weighing out 15 milligrams of carbodiimide (obtained from Polysciences, Inc.) and dissolving it in 0.75 milliliters of phosphate buffer. To the redispersed pellet, 0.6 milliliters of the carbodiimide solution was added drop wise. Thereafter, the solution and pellet were mixed for 30 minutes at room temperature on a shaker that provided end-to-end mixing. The mixed contents were centrifuged for 6 minutes, with the resulting supernatant being discarded. The pellet was resuspended in a borate buffer (obtained from Polysciences, Inc.) and centrifuged, with the supernatant again being discarded. The pellet was resuspend in 1.2 milliliters of the borate buffer and sonicated for 5 minutes.

800 micrograms of a thiolated, monoclonal antibody to C-reactive protein (obtained from BiosPacific, Inc.) was then added to the resuspended pellet and left overnight at room temperature with gentle end-to-end mixing. Thereafter, the mixture was centrifuged for 10 minutes. The supernatant was discarded or retained for protein determination using UV/Vis at 280 nanometers. The resulting pellet was then resuspended in 1 milliliter of 0.1 molar ethanolamine (obtained from Polysciences, Inc.) and mixed gently for 15 minutes at room temperature. This step served to block the unreacted sites on the microparticles. The suspension was centrifuged for 6 minutes, with the supernatant being discarded. Finally, the pellet was resuspended in 1 milliliter of a storage buffer to a final concentration of 1.25% solids.

Example 2

The ability to form a diffraction-based assay device with the conjugated hollow particles of Example 1 was demonstrated.

A gold-coated plastic film obtained from CP Films, Inc. of Canoga Park, Calif. was initially provided. The film included about 10 nanometers in thickness of gold on one side of a MYLAR film (thickness of 7 mils) so that the resulting film had a resistance of less than or equal to 13 ohms/square. The film was soaked in a 5-milligram per milliliter solution of β-casein (a blocking agent). The solution of was prepared by dissolving 25 milligrams of β-casein in 5 milliliters of phosphate buffered saline (PBS) at a pH of 7.2. After exposure to the β-casein solution for 10 minutes, the film was rinsed with distilled water and dried in an air stream. The treated film, gold-side up, was then contact-printed with a thiolated, monoclonal antibody to C-reactive protein (obtained from BiosPacific, Inc.) in 10-micron diameter circles on the film to provide a patterned x-y array of the antibody on the film. Next, the hollow particles of Example 1 were re-suspended in phosphate buffered saline [PBS] at a pH of 7.2, which contained Triton X-100 at a concentration of 0.3%.

A test sample of CRP antigen was prepared at a concentration of 50 micrograms per milliliter, and 34 microliters of the test sample was added to the top of the film. Simultaneously, 34 microliters of a control test sample was added to another piece of the contact-printed gold/mylar surface. After incubation for 5 minutes at room temperature, an 11-microliter aliquot of the re-suspended hollow particles was added to all the samples. After incubation for 10 minutes, a nitrocellulose wicking pad (obtained from Millipore, inc. 8-micrometers pore size) was placed on the hollow particles, and the antigen mixed on the patterned film (still gold-side up on film). This caused the test sample to be wicked radially away from the gold-coated surface as it was taken in or absorbed by the wicking pad. After the liquid sample had been absorbed by the wicking pad, a clear path for viewing diffraction (or lack thereof) remained through the hole cut from the wicking pad. The wicking pad had a 1.6-millimeter hole cut in its center using a die punch prior to placing it on the film. This small area was not applied with the wicking pad to provide a viewing area for diffraction from the sample.

The above steps provided a three-step diagnostic device. Diffraction was monitored by passing a red helium-neon laser (wavelength of 633 nanometers) through the film. 3 orders of diffraction were determined to be present in the positive or CRP-spiked sample, thereby indicating a high level of analyte.

Example 3

The ability to form a diffraction-based assay device with the conjugated hollow particles of Example 1 was demonstrated.

A gold-coated plastic film obtained from CP Films, Inc. of Canoga Park, Calif. was initially provided. The film included about 10 nanometers in thickness of gold on one side of a MYLAR film (thickness of 7 mils) so that the resulting film had a resistance of less than or equal to 13 ohms/square. The film was soaked in a 5-milligram per milliliter solution of β-casein (a blocking agent). The solution of was prepared by dissolving 25 milligrams of β-casein in 5 milliliters of phosphate buffered saline (PBS) at a pH of 7.2. After exposure to the β-casein solution for 10 minutes, the film was rinsed with distilled water and dried in an air stream. The treated film, gold-side up, was then contact-printed with a thiolated, monoclonal antibody to C-reactive protein (obtained from BiosPacific, Inc.) in 10-micron diameter circles on the film to provide a patterned x-y array of the antibody on the film. Next, the hollow particles of Example 1 were re-suspended in phosphate buffered saline [PBS] at a pH of 7.2, which contained 10 wt % sucrose and a heterophilic blocking reagent (obtained from Scantibodies, Inc. of Santee, Calif.) in a HBR-to-particle suspension volume/volume ratio of 1:3.

An 11-microliter aliquot of the re-suspended hollow particles was added to the patterned film using a pipette. The film was placed in a freezer at about −20° C. until the particle suspension was frozen (typically >1 hour), and then freeze-dried in a Labconco freeze drying unit (with a vacuum pump, about 5 to 20 mm Hg) to dry the hollow particles on the patterned film surface. The above provided a two-step diagnostic device. For testing, 34 microliters of a test sample, i.e., 3.4 microliters CRP-free whole blood with EDTA as anti-coagulant, diluted in 30.6 microliters of PBS with 0.3% Triton, was added to the hollow particles pre-dried on the film. This whole blood had either been spiked with C-reactive protein (e.g., 50 micrograms per milliliter, for final concentration of 5 micrograms per milliliter after dilution) to serve as a positive sample, or left "as is" to serve as the negative control. After an incubation period of 10 minutes, a nitrocellulose wicking pad (obtained from Millipore, inc. 8-micrometers pore size) was placed on the hollow particles, and the antigen mixed on the patterned film (still gold-side up on film). The wicking pad had a 1.6-millimeter hole cut in its center using a die punch prior to placing it on the film. This small area was not applied with the wicking pad to provide a viewing area for diffraction from the sample. After the liquid sample was absorbed by the wicking pad, a clear path for viewing diffraction remained through the hole cut from the wicking agent.

The above steps provided a two-step diagnostic device. Diffraction was monitored by passing a red helium-neon laser (wavelength of 633 nanometers) through the film. 3 orders of diffraction were determined to be present from the positive sample, thereby indicating a high level of analyte.

Example 4

The ability to form a diffraction-based fluidics assay device with the conjugated hollow particles of Example 1 was demonstrated.

A gold-coated plastic film obtained from CP Films, Inc. of Canoga Park, Calif. was initially provided. The film included about 10 nanometers in thickness of gold on one side of a MYLAR film (thickness of 7 mils) so that the resulting film had a resistance of less than or equal to 13 ohms/square. A fresh pipette tip was used to spread out 100 microliters of a thiolated, monoclonal antibody to C-reactive protein (obtained from BiosPacific, Inc.). The antibody solution was spread as evenly as possible over the gold/MYLAR surface. The antibody was allowed to incubate for 10 minutes on the film's surface. The inked film was then rinsed with deionized water for 10 seconds and air dried with filtered air. The antibody-inked film was placed, gold side up, in a 5-inch square vacuum chuck. Using a cheese cloth, the photo mask was wiped to remove dust and streaks. The vacuum pump was turned on to approximately 14 pounds per square inch and the film/mask set-up was sealed with a PDMS gasket. A collimating lens (convex lens) was placed on top of the photo mask and gasket, and this entire setup was then placed 8.4 inches from a laser lamp source (225 nanometers) and exposed for 2 minutes. The areas not exposed to UV light were marked and cut out from the film. The remaining patterned film was then cut into the desired size for later use.

Next, the hollow particles of Example 1 were re-suspended in phosphate buffered saline [PBS] at a pH of 7.2, which contained 10 wt % sucrose and a heterophilic blocking reagent (obtained from Scantibodies, Inc. of Santee, Calif.) in a HBR-to-particle suspension volume/volume ratio of 1:3. The particles were striped onto the patterned film using a Kinematic module Matrix 1600™ (set to a platen speed of 7 centimeters per second) at a dispense rate of 0.9 microliters per centimeter. The pump was initially purged, which allows the particle suspension to flow through the tubing to the nozzle head. The striping distance was adjusted to meet the length of the film, and lined up to ensure that striping was done down the center of the film.

After full-length striping, the film was placed immediately into a freezer at −20° C. to freeze the particle suspension, e.g., about 1 hour or more. The film was then freeze-dried for 18 hours while on flat ice packs (about 5 to 20 mm Hg, using Labconco Model #77500 freeze drying unit with a vacuum pump). The sample was then removed and placed in a low humidity chamber (e.g. <30% relative humidity).

A fluidics assay device was then formed from the above-mentioned hollow-particle printed film. The fluidics assay was cast from etched silicon masters or photoresist-made masters with polydimethylsiloxane (PDMS) (Sylgard 184 from Dow Chemical, Co.). The fluidic channels contained a 400-micron inlet channel with 92 wicks at 50 microns each. The hollow particle-printed film was removed from the freeze-dryer and cut to fit the PDMS fluidic assay, i.e., 2 centimeters×2 centimeters. The PDMS fluidic assay was mounted on the film in a manner that aligned the hollow particles along the fluidics inlet channel and central detection zone.

A 1-microliter aliquot of diluted blood (e.g., 1 part whole blood with EDTA as anti-coagulant in 9 parts diluent containing phosphate buffer solution (PBS) at pH 7.2 with Triton X-100 at 0.3%) was then placed at the entrance of the inlet channel. The whole blood was either left "as is" to serve as a negative control, or spiked with 10 to 50 micrograms per milliliter C-reactive protein (e.g., corresponding to 1 to 5 micrograms per milliliter CRP after dilution). The blood aliquot was allowed to flow up to the central detection zone area via capillary action, and finally through the wicks of the fluidic assay. Incubation/wicking times, i.e., the time for fluid to enter the inlet channel and then evacuate the central detection zone, generally ranged from 30 seconds to 8 minutes. Diffraction was monitored by passing a red helium-neon laser (wavelength of 633 nanometers) through the film. 3 or more orders of diffraction were determined to be present from the positive sample, thereby indicating a high level of analyte.

Example 5

The ability to conjugate and label hollow particles in accordance with the present invention was demonstrated. Initially, 500 microliters of SunSphere™ hollow particles (available from Rohm & Haas) were washed twice with 1 millimeter of 2-(N-morpholino) ethane sulfonic acid (pH of 5.3). Thereafter, 30 milligrams of carbodiimmide was added to the hollow particle/buffer solution. The compounds were allowed to react for 10 minutes under constant rotation.

The hollow particles were separated from the reaction solution and washed with 1 millimeter of a borated buffer. 1 milligram of fluorescent dye (5-(and-6)-((N-(5-aminopentyl)amino)carbonyl)tetramethylrhodamine (tetramethylrhodamine cadaverine) was added to 1 millimeter of the hollow particle/borate buffer solution. The compounds were allowed to react for 1 hour under constant rotation. After the reaction was complete, the supernatant was discarded and the hollow particles were washed with borate buffer until the supernatant solution became clear. The hollow particles were then re-suspended into 1 millimeter of borate buffer. From this solution, 100 microliters were removed and diluted in 500 microliters of borate buffer. 100 microliters of monoclonal antibody Mab5811 (BiosPacific, Inc., 6.4 milligrams per milliliter) was added to the hollow particle solution and allowed to react under constant rotation for over 56 hours. The reaction was quenched with 200 microliters of ethanolamine, and the hollow particles were then washed with a PBS buffer and stored in 500 milliliters of a storage buffer that contained 0.1 molar PBS, 0.15 molar NaCl, 1% BSA, 5% glycerol and 0.1% $NaN_3$.

Example 6

The ability to form a lateral flow assay device with the hollow particles of Example 5 was demonstrated.

A nitrocellulose porous membrane (HF 120 from Millipore, Inc.) having a length of approximately 30 centimeters was laminated onto supporting cards. CelQuat™ 100-H (a cellulosic polyelectrolytic derivative available from National Starch & Chemical, Inc.) was stripped onto the membrane to form a control line. In addition, monoclonal antibody for C-reactive protein (Mab 5804 obtained from BiosPacific, Inc., concentration of 1 milligram per milliliter) was immobilized on the porous membrane to form a detection line. The membrane samples were then dried for 1 hour at a temperature of 37° C. A cellulosic fiber wicking pad (Millipore, Inc. Co.) was attached to one end of the membrane and cut into 4-millimeter half strips. The half stick strips were put into various micro-wells containing 20 microliters of the fluorescent hollow particles of Example 5 and 20 microliters of CRP antigen solutions or 20 microliters of TBS buffer. The sample containing only TBS buffer was used as a negative control, while the samples containing the CRP antigen in TBS were used as test samples.

Upon completion of the assay, the half stick was removed from the micro-well and the fluorescent intensity was then measured on the detection line using a Fluorolog III Spectrofluorometer (SPEX Industries, Inc., Edison, N.J.) with a right angle mode. The results are shown below in Table I, wherein "I" represents the measured signal intensity from the fluorescent hollow particles.

TABLE I

Signal Intensity Results

| Analyte (nanograms per milliliter) | Signal Intensity "I" |
|---|---|
| 0 (control) | 44 |
| 5 | 115 |
| 50 | 160 |
| 500 | 240 |

The signal intensity for the control was considered background and did not represent any significant analyte concentration. In practice, this background intensity would be subtracted from all measured results.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An assay device for detecting an analyte in a test sample, the assay device comprising:
a porous membrane that defines a detection zone, wherein a biological receptive material is immobilized within the detection zone; and
detection probes that contain latex particles having an average size of from about 0.1 nanometer to about 100 microns, wherein the latex particles individually define a polymeric shell about a hollow interior constituting at least about 20% of the spatial volume occupied by the particle, wherein the polymeric shell of the latex particles comprises an organic polymer covalently conjugated with a specific binding member for the analyte, wherein the organic polymer is covalently conjugated with the specific binding member via a carboxylic functional group on the organic polymer, and wherein any remaining activated carboxylic functional groups on the organic polymer of the polymeric shell are blocked;
wherein the detection probes are capable of generating a detection signal when present within the detection zone.

2. The assay device of claim 1 wherein the hollow interior constitutes at least about 30% of the spatial volume occupied by the particle.

3. The assay device of claim 1, wherein the average size of the latex particles ranges from about 1 nanometer to about 10 microns.

4. The assay device of claim 1, wherein the organic polymer has a glass transition temperature that is greater than about 50° C.

5. The assay device of claim 1, wherein the organic polymer is formed one or more ethylenically unsaturated monomers.

6. The assay device of claim 1, wherein the latex particles have a spherical shape.

7. The assay device of claim 1, wherein the latex particles are monodispersed.

8. The assay device of claim 1, wherein the organic polymer is covalently conjugated with the specific binding member via an amide bond.

9. The assay device of claim 8, wherein the organic polymer is covalently conjugated with the specific binding member via the carboxylic functional group on the organic polymer after activation of the carboxylic functional group using carbodiimide and subsequent reaction with an amino group of an antibody to form the amide bond.

10. The assay device of claim 9, wherein any remaining activated carboxylic functional groups on the organic polymer of the polymeric shell are blocked with ethanolamine.

11. The assay device of claim 1, wherein the covalent conjugation with the specific binding member is accomplished using carboxylic, amino, aldehyde, bromoacetyl, idodacetyle, thiol, or epoxy functional groups.

12. The assay device of claim 1, wherein the specific binding member comprises an immunoreactive specific binding member.

13. The assay device of claim 12, wherein the immunoreactive specific binding member comprises an antigen, hapten, aptamer, antibody, or complexes thereof.

14. The assay device of claim 12, wherein the immunoreactive specific binding member comprises an antigen.

* * * * *